United States Patent
Meister et al.

(10) Patent No.: US 10,776,643 B1
(45) Date of Patent: Sep. 15, 2020

(54) VEHICULAR AIRBORNE PARTICULATE MATTER DETECTION SYSTEM

(71) Applicant: Robert Bosch GmbH, Stuttgart (DE)

(72) Inventors: Dietmar Meister, Cupertino, CA (US); Stefan Weissert, Detroit, MI (US); Soeren Wildemann, Novi, MI (US)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 16/553,349

(22) Filed: Aug. 28, 2019

(51) Int. Cl.
| | | |
|---|---|---|
| *G06K 9/00* | (2006.01) | |
| *G01N 21/53* | (2006.01) | |
| *G01N 33/00* | (2006.01) | |
| *H04N 7/18* | (2006.01) | |
| *G08B 3/10* | (2006.01) | |

(52) U.S. Cl.
CPC ......... *G06K 9/00832* (2013.01); *G01N 21/53* (2013.01); *G01N 33/0036* (2013.01); *G01N 33/0063* (2013.01); *G08B 3/10* (2013.01); *H04N 7/188* (2013.01); *G01N 2201/062* (2013.01)

(58) Field of Classification Search
CPC .............. G06K 9/00832; H04N 7/188; G01N 33/0063; G01N 21/53; G01N 33/0036; G01N 2201/062; G08B 3/10
See application file for complete search history.

(56) References Cited

U.S. PATENT DOCUMENTS

| 5,190,307 A | * | 3/1993 | Brown | B60R 99/00 180/271 |
| 2018/0073759 A1 | * | 3/2018 | Zhang | G05B 17/02 |
| 2018/0186212 A1 | * | 7/2018 | Kundu | A61L 9/015 |

FOREIGN PATENT DOCUMENTS

DE 102012021505 A1 * 5/2014 ......... B60H 1/00864

OTHER PUBLICATIONS

Invernizzi G. et al. "Residual tobacco smoke: measurement of its washout time in the lung and of its contribution to environmental tobacco smoke", Tobacco Control 2007; 16: 29-33. Doi: 10.1136/tc.2006.017020 (Year: 2007).*

* cited by examiner

*Primary Examiner* — Richard A Hansell, Jr.

(74) *Attorney, Agent, or Firm* — Maginot, Moore & Beck LLP (57) ABSTRACT

A vehicular airborne particulate detection system in one embodiment includes a particulate matter concentration sensor positioned in a passenger space of a vehicle. The particulate matter concentration sensor generates a signal associated with an airborne particulate matter concentration in the passenger space which is analyzed by a controller to identify a cyclical particulate matter concentration pattern which is classified as a smoking event. The controller then generates an output using a user interface based upon the classified smoking event.

18 Claims, 5 Drawing Sheets

VEHICULAR AIRBORNE PARTICULATE MATTER DETECTION SYSTEM

TECHNICAL FIELD

This disclosure relates generally to airborne particulate matter detection and more particularly to airborne particulate matter concentration detection in vehicles.

BACKGROUND

Vehicles such as automobiles, trucks, buses, vans, ferries, etc. are frequently used by more than one individual either at the same time or sequentially. For example, a bus or shuttle will typically include a number of passengers at one time while a fleet vehicle or rental vehicle may be used by a single individual at a time, but by different drivers for different trips. In either instance, it is not uncommon for the owner/operator of the vehicle to prohibit smoking in the vehicle since the smoke is detrimental to the health not only of the individual smoking but to others in the vehicle. Moreover, the odor that remains in the vehicle makes the vehicle less desirable for future users of the vehicle.

In a scenario with a bus driver and a number of passengers, the bus driver can enforce a ban on smoking. When the vehicle is, e.g., a rental vehicle, there may not be an individual in the vehicle to enforce the ban on smoking. Moreover, as self-driving vehicle technology matures and the industry evolves toward level 5 autonomous driving, new business models can be expected to develop. These new business models may include self-driving taxis and shuttles.

Accordingly, these vehicles will be shared among strangers, like any other public transportation, and will not have a mechanism for monitoring/enforcing a ban on smoking.

If smoking does occur in a vehicle which is shared amongst multiple individuals, the owner of the vehicle is frequently left with the expense of fumigating the passenger space of the vehicle. It would be beneficial to be able to pass this cost on to the individuals responsible for the smoking. In a vehicle which is simultaneously shared amongst strangers, however, it can be difficult to identify which of the strangers is responsible for the smoking event.

What is needed therefore is a system which automatically detects smoking in a passenger space of a vehicle. It would be beneficial if the system could be used to positively identify the individual responsible for the smoking event. It would be further beneficial for such a system to provide a warning to occupants of the vehicle that smoking had been detected so as to prompt the occupant(s) to cease smoking.

SUMMARY

According to one embodiment, one or more of the foregoing needs is addressed by a vehicular airborne particulate matter detection system including a first particulate matter concentration sensor positioned in a passenger space of a vehicle. The first particulate matter concentration sensor generates a first signal associated with an airborne particulate matter concentration in the passenger space. The system further includes a user interface, a memory including program instructions stored therein, and a controller operably connected to the first particulate matter concentration sensor, the user interface, and the memory. The controller executes the program instructions to obtain the first signal, identify a cyclical particulate matter concentration pattern based upon the obtained first signal, classify the cyclical particulate matter concentration pattern as a smoking event, and generate an output using the user interface based upon the classified smoking event.

In one or more embodiments, the system includes a second particulate matter concentration sensor operably connected to the controller and positioned in the passenger space of the vehicle, the second particulate matter concentration sensor configured to generate a second signal associated with the airborne particulate matter concentration in the passenger space. In such embodiments, the first particulate matter concentration sensor is preferably located in an upper forward region of the vehicle and the second particulate matter concentration sensor is preferably located in an upper rearward region of the vehicle. The controller is further configured to execute the program instructions to obtain the second signal, and identify the cyclical particulate matter concentration pattern based upon the obtained second signal.

In one or more embodiments, the system includes a third particulate matter concentration sensor located outside of the passenger space which is configured to generate a third signal associated with airborne particulate matter concentration outside of the passenger space. The controller is further configured to execute the program instructions to obtain the third signal, establish an airborne particulate matter concentration threshold based upon the obtained third signal, and identify the cyclical particulate matter concentration pattern based upon the established airborne particulate matter concentration threshold.

In one or more embodiments, the user interface includes a speaker and the controller is configured to execute the program instructions to generate an audible output using the speaker based upon classifying the cyclical particulate matter concentration pattern as a smoking event.

In one or more embodiments, the user interface includes a display and the controller is configured to execute the program instructions to generate a visual output using the display based upon classifying the cyclical particulate matter concentration pattern as a smoking event.

In some embodiments the user interface includes both a speaker and a display to provide both audio and visual alerts to individuals in the passenger space that smoking is not allowed.

In one or more embodiments at least a portion of the user interface is located remotely from the vehicle.

In one or more embodiments the system includes a camera operably connected to the controller and the memory. In such embodiments the controller is configured to execute the program instructions to capture an image of the passenger space using the camera based upon classifying the cyclical particulate matter concentration pattern as a smoking event, and store the captured image in the memory.

In one or more embodiments, the system includes an airborne particulate matter concentration threshold stored in the memory which in some embodiments is established by the controller, and a camera operably connected to the controller and the memory. The controller is configured to execute the program instructions to compare the obtained first signal to the stored airborne particulate matter concentration threshold, capture an image of the passenger space using the camera based upon the comparison, analyze the captured image, and classify the cyclical particulate matter concentration pattern as a smoking event based upon the analyzed image.

In one or more embodiments the vehicle includes a window movable between a closed position and at least one open position, and a window control unit configured to both move the window between the closed position and the at least one open position, and to generate a fourth signal associated with a position of the window. In such embodiments, the controller is configured to execute the program instructions to receive the fourth signal from the window control unit, establish an airborne particulate matter concentration threshold based upon the obtained fourth signal, and identify the cyclical particulate matter concentration pattern based upon the established airborne particulate matter concentration threshold.

According to one embodiment, one or more of the foregoing needs is addressed by operating a vehicular airborne particulate matter detection system by generating with a first particulate matter concentration sensor positioned in a passenger space of a vehicle a first signal associated with an airborne particulate matter concentration in the passenger space. The method includes executing with a controller program instructions stored in a memory to obtain the first signal, identify a cyclical particulate matter concentration pattern based upon the obtained first signal, classify the cyclical particulate matter concentration pattern as a smoking event, and generate an output using the user interface based upon the classified smoking event.

In one or more embodiments the method includes generating with a second particulate matter concentration sensor positioned in the passenger space of the vehicle a second signal associated with the airborne particulate matter concentration in the passenger space. The method further includes executing the program instructions with the controller to obtain the second signal, and to identify the cyclical particulate matter concentration pattern based upon the obtained second signal.

In one or more embodiments the method includes generating with a third particulate matter concentration sensor positioned outside of the passenger space of the vehicle a third signal associated with the airborne particulate matter concentration in the passenger space. The method further includes executing the program instructions with the controller to obtain the third signal, to establish an airborne particulate matter concentration threshold based upon the obtained third signal, and to identify the cyclical particulate matter concentration pattern based upon the established airborne particulate matter concentration threshold.

In one or more embodiments executing the program instructions with the controller to generate the output includes executing the program instructions with the controller to generate an audible output using a speaker of the user interface based upon classifying the cyclical particulate matter concentration pattern as a smoking event.

In one or more embodiments executing the program instructions with the controller to generate the output includes executing the program instructions with the controller to generate a visual output on a display of the user interface based upon classifying the cyclical particulate matter concentration pattern as a smoking event.

In one or more embodiments executing the program instructions with the controller to generate the output includes transmitting the output to a portion of the user interface located remotely from the vehicle.

In one or more embodiments the method includes executing the program instructions with the controller to control a camera operably connected to the controller to capture an image of the passenger space based upon classifying the cyclical particulate matter concentration pattern as a smoking event, and to store the captured image in the memory.

In one or more embodiments the method includes generating with a window control unit configured to move a window of the vehicle between a closed position and at least one open position a fourth signal associated with a position of the window. The method further includes executing the program instructions with the controller to receive the fourth signal from the window control unit, and to establish an airborne particulate matter concentration threshold based upon the obtained fourth signal. In such embodiments executing the program instructions with the controller to identify the cyclical particulate matter concentration pattern includes executing the program instructions with the controller to identify the cyclical particulate matter concentration pattern based upon the established airborne particulate matter concentration threshold.

DETAILED DESCRIPTION

For the purposes of promoting an understanding of the principles of the embodiments described herein, reference is now made to the drawings and descriptions in the following written specification. No limitation to the scope of the subject matter is intended by the references. This disclosure also includes any alterations and modifications to the illustrated embodiments and includes further applications of the principles of the described embodiments as would normally occur to one skilled in the art to which this document pertains.

Various operations may be described as multiple discrete actions or operations in turn, in a manner that is most helpful in understanding the claimed subject matter. However, the order of description should not be construed as to imply that these operations are necessarily order dependent. In particular, these operations in some embodiments are performed in a different order than the described embodiment. Various additional operations are performed and/or described operations are omitted in additional embodiments.

The terms "comprising," "including," "having," and the like, as used with respect to embodiments of the disclosure, are synonymous. As used herein, the word "about" when modifying a number means at least within ten percent of the stated number, preferably within five percent of the stated number, and most preferably within two percent of the stated number.

The embodiments of the disclosure discussed below are applicable to any desired airborne particulate sensor which can produce a signal related to a sensed particulate matter concentration. As used herein, a "smoking event" is an event wherein airborne particulate matter is cyclically introduced into the passenger space of a vehicle. Accordingly, vaping, cigarette smoking, pipe smoking, cigar smoking, and the like which generate a cyclical introduction of particulate matter into the passenger space of a vehicle are "smoking events". A fire is not a cyclical event.

Figure 1:
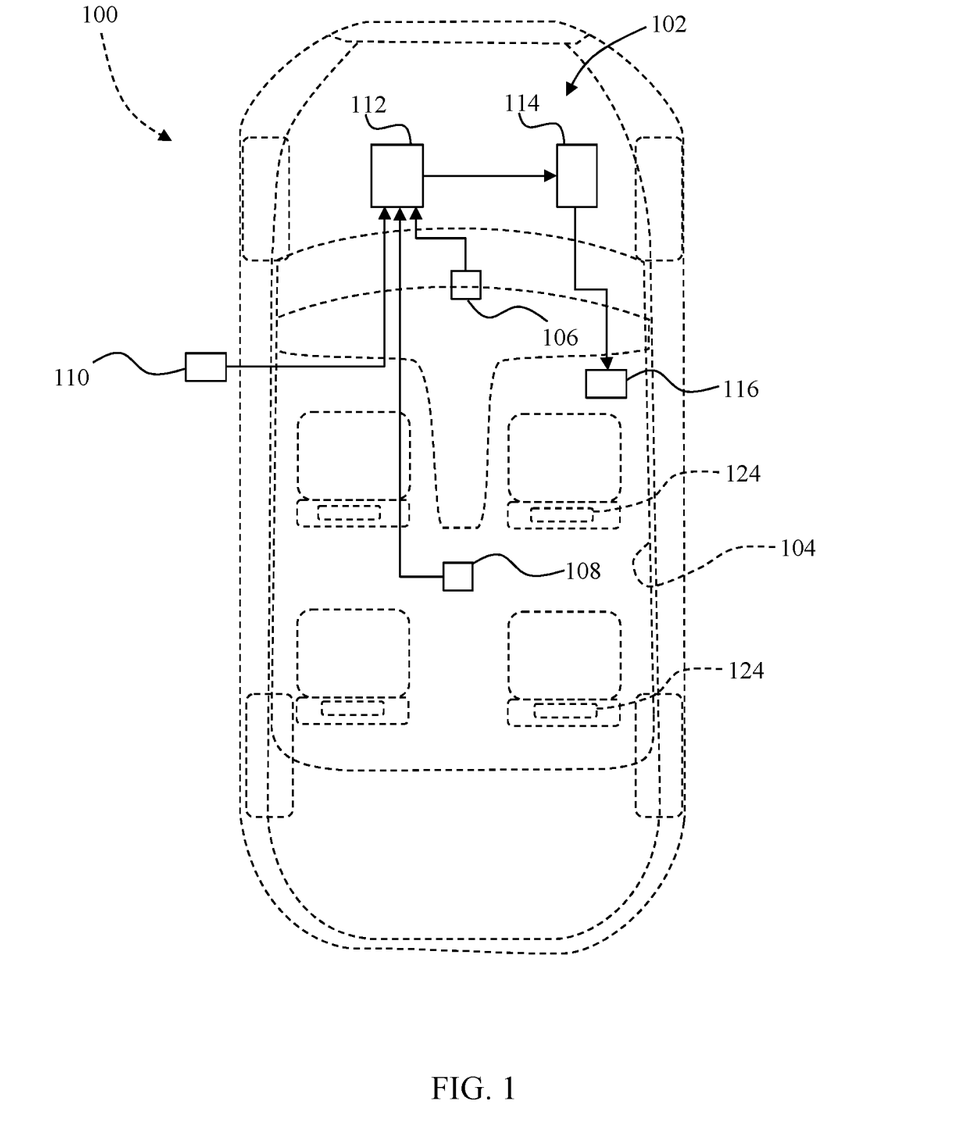
FIG. 1 is a schematic view of a vehicle including a vehicular airborne particulate matter detection system according to the disclosure.
Figure 2:
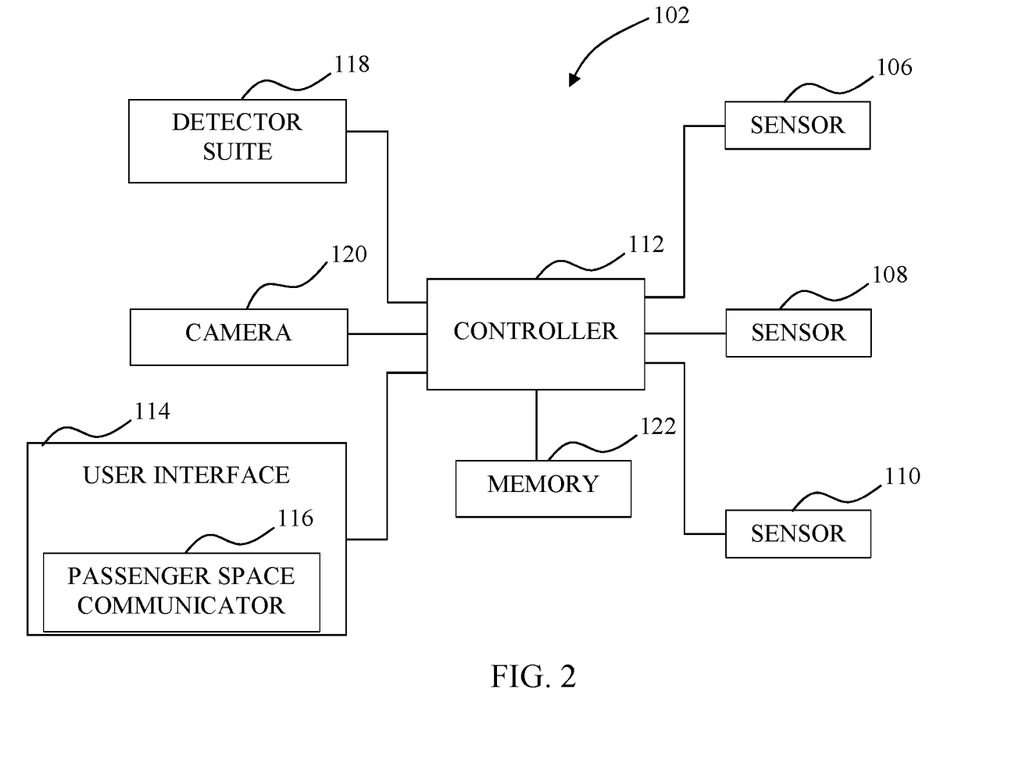
FIG. 2 is a schematic view of the vehicular airborne particulate matter detection system of FIG. 1.

Referring now to FIG. 1, a vehicle 100 includes a vehicular airborne particulate detection system 102 which is at least partially located within a passenger space 104. The vehicular airborne particulate detection system 102 in this embodiment includes two airborne particulate matter concentration sensors 106 and 108 which are located within the passenger space 104. In the embodiment of FIG. 1, a third airborne particulate matter concentration sensor 110 is located outside of the passenger space 104. The airborne particulate matter concentration sensors 106, 108, and 110 are each operably connected to a controller 112. The controller 112 is in turn operably connected to a user interface 114 which in this embodiment includes a passenger space communicator 116. The vehicular airborne particulate detection system 102 further includes a detector suite 118, a camera 120, and a memory 122 as shown in FIG. 2. Operable connection between the various components in different embodiments is accomplished wirelessly, using wired connections, or a combination of wired and wireless connections.

The airborne particulate matter concentration sensors 106, 108, 110 may any desired particulate matter concentration sensor or combination of sensors which can provide signals related to an airborne particulate matter concentration. In one embodiment, one or more of the sensors is a sensor utilizing an LED in combination with a photodiode. Preferably the airborne particulate matter concentration sensors 106, 108, 110 can detect and distinguish between particulate matter with particle diameter up to one micron (PM1), and/or 2.5 microns (PM2.5), and/or 10 microns (PM10). In some embodiments, the airborne particulate matter concentration sensors do not distinguish between particles of different diameters. For example, in some embodiments a PM2.5 sensor provides an output related to the particulate matter concentration of particulate matter of up to 2.5 microns. One acceptable sensor is the particulate matter concentration sensor model SPS30 commercially available through Sensirion AG of Staefa, Switzerland. While there are three airborne particulate matter concentration sensors 106, 108, 110 depicted in the embodiment of FIG. 1, in other embodiments there is a single airborne particulate matter concentration sensor located solely in the passenger space 104. In other embodiments there are more than two airborne particulate matter concentration sensors located in the passenger space 104.

Typically it is preferred to position at least one of the airborne particulate matter concentration sensors in a location favorable for detection of airborne particulate matter exhaled from an individual within the passenger space 104. Accordingly, in embodiments with a single airborne particulate matter concentration sensor, the airborne particulate matter concentration sensor is preferably positioned in an upper region of the passenger space 104. An "upper region" is a region in the passenger space 104 which is at or above the level of a headrest 124 (see FIG. 1). The single airborne particulate matter concentration sensor may thus be positioned at or near an overhead light, a rearview mirror, etc. In embodiments with multiple airborne particulate matter concentration sensors, in addition to or as an alternative to the foregoing positions, one or more airborne particulate matter concentration sensors are positioned in the headrests 124 of the forward seats.

The controller 112 is implemented in various embodiments with one or more general or specialized programmable processors that execute programmed instructions which are stored in the memory 122. In some embodiments at least some of the functionality of the controller 112 is provided by a vehicular control system and/or remotely from the vehicle 100 such as by a remote controller located at a vehicle fleet management center, a service center, a manufacturing center, etc. Thus, in some embodiments, the controller 112 is embodied as multiple controllers which are located in the vehicle 100 and/or remotely from the vehicle 100.

The program instructions and data required to perform the programmed functions described herein are stored in the memory 122. In some embodiments, the memory 122 is embodied as a plurality of memories which in some embodiments include one or more memories remote from the vehicle 100. The processors, the memory, and interface circuitry components in various embodiments are provided on a printed circuit card or provided as a circuit in an application specific integrated circuit (ASIC). In some embodiments, the circuits are implemented with discrete components or circuits provided in VLSI circuits. The circuits described herein are also implemented in some embodiments with a combination of processors, ASICs, discrete components, or VLSI circuits.

The user interface 114 is implemented in various embodiments with one or more of a keyboard, mouse, touch display, virtual keyboard, virtual mouse, etc. In some embodiments, at least some of the functionality of the user interface is provided remotely from the vehicle 100. In some such embodiments, the user interface 114 includes a communications module configured to provide communication between the vehicle based components and the remote components.

Thus, in some embodiments, the user interface 114 is embodied as multiple components which are located in the vehicle 100 and/or remotely from the vehicle 100.

The user interface 114 in the embodiment of FIG. 1 includes the passenger space communicator 116. A "passenger space communicator" as that term is used herein means any device such as a display, speaker, etc. which provides data to an individual within the passenger space 104. In some embodiments, the passenger space communicator 116 is a PDA, cell phone, or the like which forms a communications link with the user interface 114 using, e.g., Bluetooth, WiMax, or the like.

The detector suite 118 in one embodiment includes one or more detectors configured to identify the condition of an associated window. One such detector is described in U.S. Pat. No. 5,404,673, which issued Apr. 11, 1995. Each detector provides a signal associated with the extent to which the associated window is opened.

Figure 3:
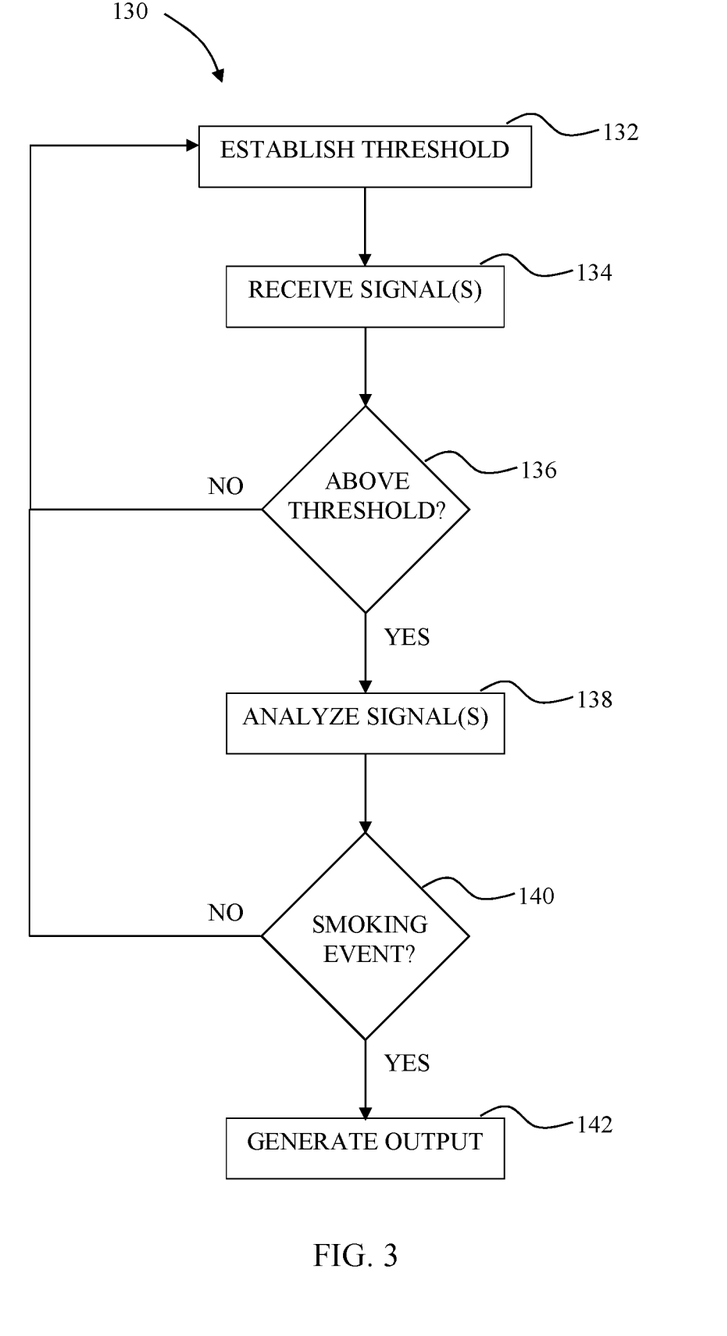
FIG. 3 depicts a flow chart of a procedure for operating the vehicular airborne particulate matter detection system of FIG. 1.

The method 130 of FIG. 3 is executed at least in part by the controller 112 executing program instructions stored in the memory 122 in one embodiment to identify a smoking event in the passenger space 104. At block 132 a threshold is established for the airborne particulate matter concentration sensors 106 and 108. The threshold in some embodiments is a fixed value stored in the memory 122. In some embodiments, each particular particulate matter size or size group has a respective threshold.

In some embodiments, the threshold is additionally or alternatively established dynamically based upon the signal from the airborne particulate matter concentration sensor 110. In particular, the controller 112 obtains the signal from the airborne particulate matter concentration sensor 110 to identify the particulate matter concentration of the environment surrounding the vehicle and applies an offset to the particulate matter concentration of the environment surrounding the vehicle to establish a threshold which in some embodiments is then stored in the memory 122. This reduces spurious classification of smoking events because of high background particulate matter caused, e.g., by smog, temperature inversions, external fires, etc. by differentiating between airborne particulate matter introduced from outside of the vehicle and airborne particulate matter introduced from within the vehicle.

In some embodiments, the threshold is additionally or alternatively established dynamically based upon a signal from one or more of the airborne particulate matter concentration sensors 106/108. In particular, as smoke and/or other airborne particulates are introduced into a vehicle, the background level of airborne particulate matter increases. Accordingly, an output from the airborne particulate matter concentration sensors 106/108 is used in setting the threshold based upon a difference between the background airborne particulate matter concentration and the airborne particulate matter concentration threshold. In these embodiments, the controller 112 is configured to eliminate data from smoking events which could artificially raise the threshold. In one embodiment this is accomplished by requiring a constant output from the airborne particulate matter concentration sensors 106/108 over a predetermined period of time. A "constant output" is an output which does not vary by more than a predetermined amount, e.g., a variation associated with a 15 µg/m$^3$ change in concentration. The predetermined length of time in one embodiment is fifty seconds.

In some embodiments, the window position and other vehicle attributes such as vehicle speed, fan speed, etc. are further assessed by the controller 112 in determining the threshold. Accordingly, even when external particulate matter concentration is high, if all of the windows are shut and the vehicle is equipped with an air filter for incoming air, the threshold offset may be a negative offset.

Once the threshold is established, the controller 112 at block 134 receives at least one signal from an airborne particulate matter concentration sensor located in the passenger space 104 such as one or more of the airborne particulate matter concentration sensors 106 and 108. At block 136 the controller 112 determines if the received signal(s) indicate that airborne particulate matter concentration in the particle size(s) of interest is above the threshold. If the airborne particulate matter concentration in the particle size(s) of interest is below the threshold, then the method continues monitoring at block 132. If at block 136 the airborne particulate matter concentration in the particle size(s) of interest is above the threshold, the method continues to block 138 and the signal is analyzed.

As will be discussed in further detail below, signal analysis at block 138 is directed to identifying a cyclical airborne particulate matter concentration pattern using the signal(s) from the airborne particulate matter concentration sensor(s). A cyclical pattern is used to distinguish a smoking event from a fire or an increase in background airborne particulate matter resulting e.g., from smog. In the case of fire, increase in smog, etc., the airborne particulate matter concentration will initially increase from below the threshold to above the threshold. The airborne particulate matter concentration will then increase to a relatively constant steady state value at any given height in the vehicle. In the case of a fire, the steady state value is driven by the rate of the fire introducing airborne particulate matter and the removal of the airborne particulate matter due to, e.g., ventilation. For smog and other background contributors, a similar variation is observed.

In the case of smoking, however, the airborne particulate matter is introduced in a series of steps (due to exhaling) on top of a steady infusion (due to smoldering). Vaping produces a similar characteristic with step introduction of particulate matter due to exhaling particulate matter. Accordingly, the increase in airborne particulate matter is cyclical.

Moreover, while smoke tends to rise initially because it is hotter than the atmosphere into which it is injected, it rapidly cools and the particulates in the smoke then move downwardly. This results in a series increases and, depending upon the frequency of exhaling, either decreases or plateaus in the concentration of airborne particulate matter at any given height within the passenger space even when no ventilation is provided.

If ventilation is provided to the space by, e.g., a fan and/or an open window, then the decrease in airborne particulate matter concentration is amplified so long as the background airborne particulate matter concentration is less than the airborne particulate matter concentration from the smoking event. Moreover, while any distance between the smoker and the airborne particulate matter concentration sensor reduces the concentration of airborne particulate matter due to spreading of the plume, ventilation to the passenger space 104 reduces the maximum concentration of airborne particulate matter. For this reason it is beneficial to provide a number of airborne particulate matter concentration sensors, each positioned to optimally detect airborne particulate matter concentration for a particular passenger location.

Accordingly, so long as the received signal is above the threshold, the controller 112 evaluates the signal to identify a cyclical pattern at block 138. If at block 140 sufficient data has not been collected to identify a cyclical pattern in the received data, then the process continues to block 132. If, however, the controller 112 determines that the data received has remained above the threshold and exhibits a cyclical characteristic, then at block 140 the controller 112 classifies the received data as a "smoking event" and the process proceeds to block 142.

At block 142 the controller generates an output based upon classifying the received data as a smoking event. In some embodiments the generated output includes data associate with the smoking event which is then stored in memory 122, which in various embodiments is locally and/or remotely located, and retrieved at a later time. For example, the data in some embodiments is retrieved during a vehicle inspection after use of the vehicle using, e.g., the vehicles onboard diagnostic port which may be wired or wireless. This retrieved data is then used in assessing charges to the user of the vehicle for cleaning of the vehicle. In embodiments wherein at least a portion of the memory 122 is remote, the data is transmitted from the vehicle using a communications module in the controller 112 to a remote location for storage and/or further action.

The further action in some embodiments includes generation of a bill for cleaning of the vehicle. In some embodiments, actual cleaning of the vehicle does not occur after each smoking incident. In particular, while an airborne particulate matter concentration sensor may detect an increased baseline of airborne particulate matter after a smoking event due to the sensitivity of the airborne particulate matter concentration sensor, the airborne particulate matter may not be at a level which is detectable by a user of the vehicle. The effects of smoking, and other non-smoking related particles, however, are cumulative. Accordingly, to avoid unnecessary vehicle cleaning a record of each smoking event is accumulated and used as an indicator of when the vehicle should be cleaned before the cumulative effects are such that a user notices the odor. Rather than simply charge the last user, however, each user associated with a smoking event is charged to spread the costs amongst the smokers.

In some embodiments the generated output includes a warning transmitted through the user interface in the vehicle to communicate a message to the individuals in the passenger space 104. The message in some embodiments is transmitted wirelessly to, e.g., cell phones, personal digital assistants, and the like in the passenger space. In some embodiments, the passenger space communicator is in the form of a speaker and/or display and the generated output comprises a verbal and/or visual warning to the passenger space 104 to the effect that a smoking event has been detected and such activity is not allowed.

In some embodiments incorporating the camera 120, the generated output includes a control signal to the camera to obtain an image of the passenger space 104. The image is stored in the memory 122 to support the assignment of cleaning charges to one or more individuals in the passenger space. In some embodiments, the camera is in the form of a plurality of cameras to provide sufficient coverage of the passenger space 104 to identify each individual involved in the smoking event. In some embodiments a single image is taken. In other embodiments, a series of images and/or a video is obtained. In some embodiments, an image is obtained each time a local peak in particulate matter concentration is identified by the controller 112.

It is possible that in some scenarios a single image obtained after a smoking event has been identified based solely upon the airborne particulate matter concentration sensors will not reveal which individual within the vehicle was smoking since smoking is an intermittent event. Accordingly, in some embodiments the camera 120 is controlled by the controller 112 to obtain images in a continuous loop. Thus, the output generated at block 142 causes a video clip or series of images taken from before the smoking event was identified up to and/or beyond the time that the smoking event was identified to be stored in the memory 122. In one or more embodiments, the output causes a video clip or series of images taken from at least thirty seconds before the smoking event was identified up to the time that the smoking event was identified to be stored. In one or more embodiments the images are obtained at a rate of two frames per second to reduce the amount of storage needed.

One issue that arises with the use of video evidence is that there may be other occupants who are not smoking in the images and the use of such images may violate the privacy of the individual. While users of the vehicle will typically be required to permit the use of their image as a condition of entry into the vehicle, so as to limit unnecessary distribution of images of persons who are not smoking, the obtained images are processed to detect the smoker and mask out any other faces. In some embodiments this is performed autonomously by the controller prior to storing the images in the memory 122. In some embodiments, various transforms are applied to retain the information that shows smoking but obfuscate the identity of the smoker as well as all the other occupants.

Preferably, in addition to any desired obscuration or encryption of individuals, the image or images which are stored in the memory are processed to store the image which most clearly depicts the user engaged in the smoking event and/or to compress the data. Data compression is useful both in embodiments which store the image in a local memory 122 and those which transmit the data to a remote memory 122. The image or images are further preferably associated with the data from the airborne particulate matter concentration sensors.

While the camera 120 is used in some embodiments to document a smoking event, in some embodiments the camera 120 is additionally or alternatively used in identifying the smoking event at block 138. In one or more embodiment, the same software executed by the controller 112 to identify the individual smoking is likewise used to identify the smoking event. In one such embodiment, upon an initial detection of a high concentration of particulates the controller 112 executes a smoking detection algorithm which augments the signal analysis at block 138. The smoking detection algorithm in some embodiments uses one or more of facial recognition, object recognition, color analysis, energy analysis, and disorder analysis.

In some embodiments the smoking detection algorithm is used to eliminate false positive smoking event identification. By way of example, it is possible for smoke generated by an individual external to the vehicle to be detected within the vehicle due to wind conditions in combination with one or more open doors, windows, etc. By reviewing images with the smoking detection algorithm from shortly before a high concentration of airborne particulate matter is detected and establishing that no individual within the vehicle was smoking, the controller 112 eliminates false smoking event determinations.

In one or more embodiments, the method 130 is modified from the order depicted in FIG. 3 by addition to, replacement of, or omission of one or more of the blocks. By way of example, in some embodiments only a single threshold is used. Accordingly, the threshold is established only once. In some embodiments the threshold is determined only after a signal is received. In some embodiments the airborne particulate matter concentration sensor sensitivity is effectively the threshold of the system.

Figure 4:
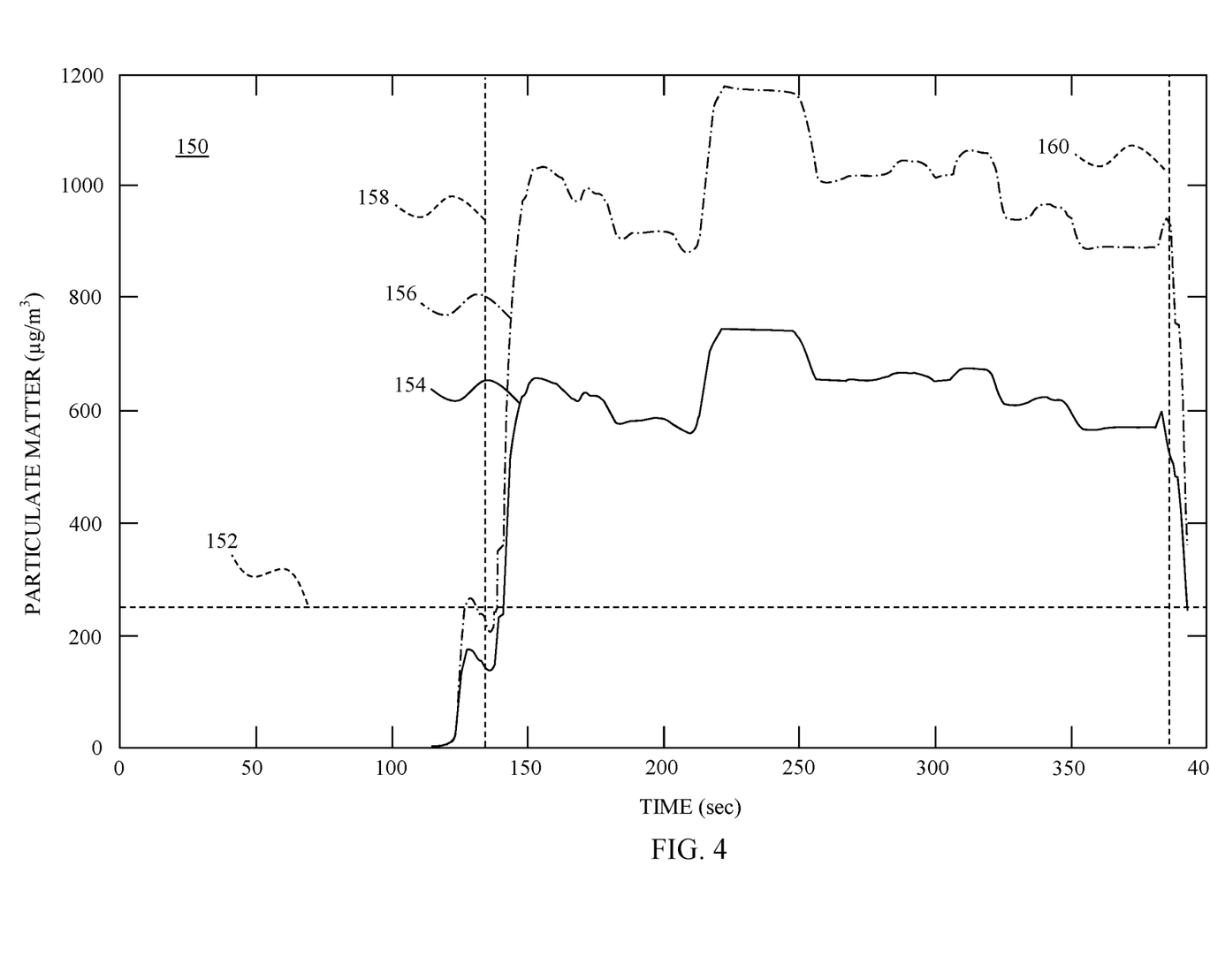
FIG. 4 is a chart of a simulation of the particulate matter concentration within a passenger space of the vehicle of FIG. 1 during a smoking event with the windows closed.

As discussed above, the controller 112 analyzes one or more signals from one or more airborne particulate matter concentration sensors in order to classify the received signals a smoking event. The manner in which classification occurs is further explained with reference to FIG. 4. FIG. 4 depicts a chart 150 of the simulated output of an airborne particulate matter concentration sensor which has been converted to particulate matter concentration in milligrams/cubic meter for a smoking event in the form of an individual vaping. Vaping was simulated for an individual in the passenger seat with the passenger window closed. The exhalant was directed straight forward and vaping was simulated at about four puffs per minute once inhaling commenced. For this simulation, a threshold of 250 $\mu g/m^3$ was used for particulate matter of up to 2.5 microns as indicated by the line 152. The line 154 depicts the concentration of particulate matter of up to 1 micron and the line 156 depicts the concentration of particulate matter of up to 2.5 microns.

At t=120 seconds, the vaping machine is energized which results in an increase in the detected particulate matter concentration. While the line 156 exceeds the threshold 152 and peaks at about t=130, the line 154 does not. Additionally, the line 156 simply decreases to below the threshold with no further increases or plateauing. Accordingly, the controller 112 does not identify this event as a "smoking event" since only one half of a cycle has been detected. At the time associated with the line 158 a first "puff" of the vaping machine is simulated and about t=140 the line 156 exceeds the threshold 152. The rapid increase in particulate matter concentration peaks at about t=152 and is followed by a gradual decrease until about t=210. Throughout the decrease, however, there are two distinct increases in the sensed particulate matter concentration. The same pattern is exhibited by the line 154. Accordingly, three cycles have been detected by time t=210.

After about t=210, the particulate matter concentration increases as indicated by both line 152 and line 154. After peaking at about t=220, a plateau is maintained until about t=250. The lines 152 and 154 then decrease, with a few plateaus and small increases, until about t=390 at which point the vaping ceases at line 160 and the particulate concentration rapidly decreases. Thus, both the PM1 line and the PM2.5 line show cyclical pattern.

Figure 5:
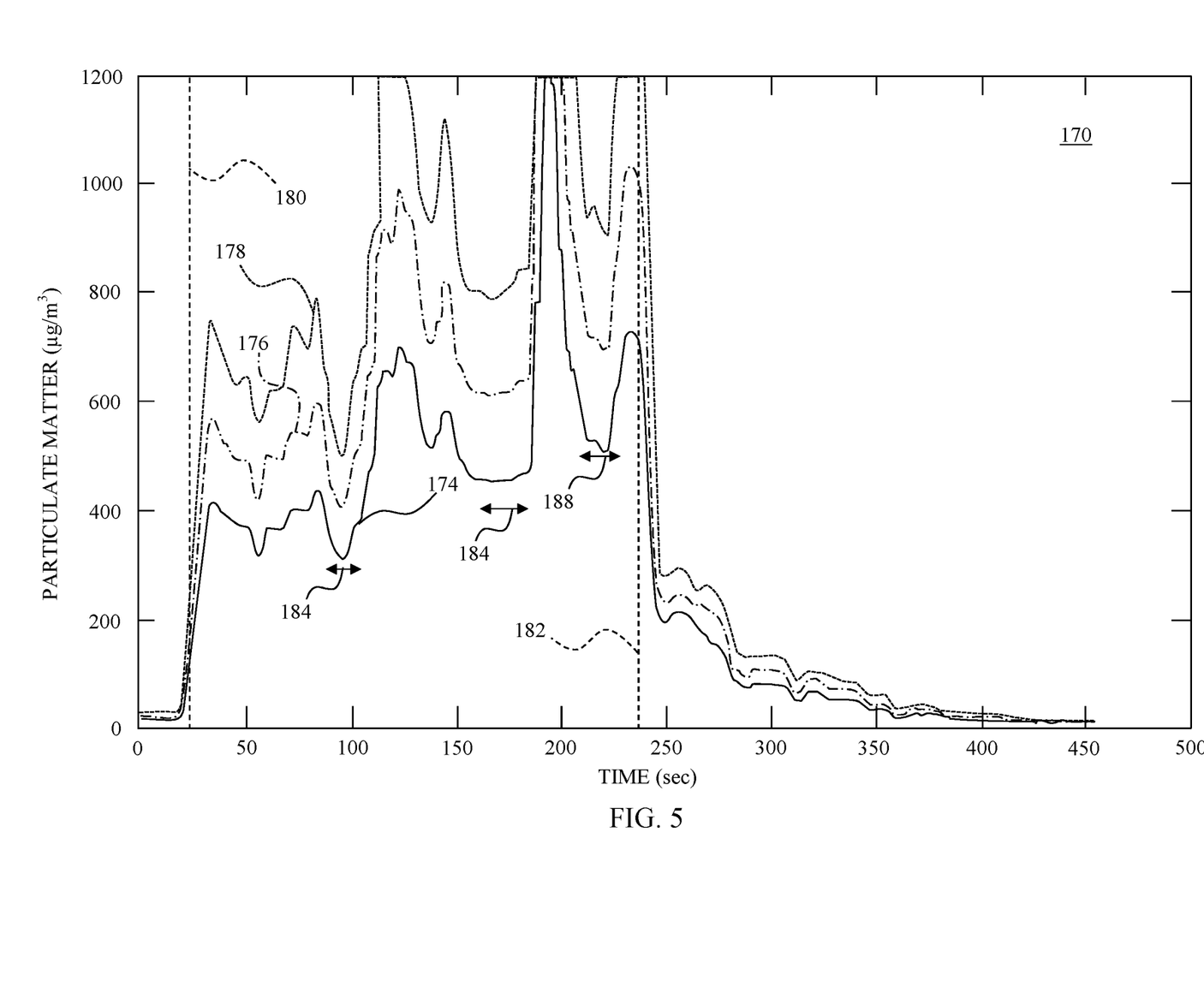
FIG. 5 is a chart of a simulation of the particulate matter concentration within a passenger space of the vehicle of FIG. 1 during a smoking event with a window opened.

FIG. 5 depicts a chart 170 of the simulated output of an airborne particulate matter concentration sensor which has been converted to particulate matter concentration in milligrams/cubic meter for a smoking event in the form of an individual smoking. Smoking was simulated for an individual in the driver's seat with the driver's window open. The exhalant was directed out of the open window, and when the vehicle is stopped during the simulation the cigarette is held outside of the passenger space through the open window. The line 174 depicts the concentration of particulate matter of up to 1 micron, the line 176 depicts the concentration of particulate matter of up to 2.5 microns and the line 178 depicts the concentration of particulate matter of up to 10 microns.

At t=20 seconds, the cigarette is lit which results in an increase in the detected particulate matter concentration. At the time associated with the line 180 a first "puff" of the cigarette is simulated and about t=35 each of the lines 174, 176, and 178 peak. From the time t=35 until about t=245 at line 182, at which point smoking is terminated, each of the lines 174, 176, and 178 exhibit extreme variations in concentration with multiple increases interspersed with decreases and plateaus. Thus, multiple cycles are detected. Some of the characteristics lines 174, 1786, and 178 are associated with period at which the vehicle is simulated as stopped (see, e.g., arrows 184, 186, and 188), and the cigarette is positioned outside of the window. After the cigarette is extinguished at about t=245, a passenger window is opened and the particulate matter concentration at all particle sizes decreases rapidly.

Accordingly, FIGS. 4 and 5 demonstrate that unlike a fire which generates a steady increase in particulate matter which eventually plateaus and then decreases, vaping creates a cyclical pattern with a number of increases, plateaus, and decreases. Moreover, the cyclical characteristic is identifiable in each of the PM1.0, the PM2.5, and the PM10 data. Thus, any one or any grouping of the particulate matter sizes are used in various embodiments to identify a cyclical pattern.

The controller 112 is thus configured in one embodiment to identify the data as a "cyclical pattern" when two periods of increase in particulate matter concentration are separated by a period of decreased particulate matter concentration or a plateaued particulate matter concentration. In various embodiments, incorrect classifications are reduced by increasing the minimum number of cycles required before establishing that a cyclical pattern exists.

Additionally, incorrect classifications in some embodiments are reduced by providing a low pass (<0.05 Hz) filtered signal for analysis and identification of local maxima and minima. In some embodiments, a minimum time span of sensor values above the threshold (which is separately identified for each particle size) is incorporated. In some such embodiments, a cyclical pattern is further identified when a plurality of individual events exceed the particulate matter concentration threshold with a pre-defined periodicity, e.g., 4 times per minute, over a predefined window, e.g., 3 minutes. This accounts for scenarios wherein a smoker has a window open and directs all of the smoke out of the window.

Furthermore, by incorporating a variety of sensors, analysis of the signals from the airborne particulate matter concentration sensors can be enhanced. For example, speed of the vehicle, fan speed, etc. have an impact on the concentration of particulate matter when a window is opened, and even more so when two are opened. Accordingly, some embodiments incorporate a window position sensor/control signal and/or vehicle speed sensor/control signal and/or fan speed sensor/control signal which is/are used to better characterize the activity within the passenger space.

Accordingly, it will be appreciated that variants of the above-described and other features and functions, or alternatives thereof, may be desirably combined into many other different systems, applications or methods. Various presently unforeseen or unanticipated alternatives, modifications, variations or improvements may be subsequently made by those skilled in the art that are also intended to be encompassed by the foregoing disclosure.

What is claimed is:

1. A vehicular airborne particulate matter detection system, comprising:
    a first particulate matter concentration sensor positioned in a passenger space of a vehicle, the first particulate matter concentration sensor configured to generate a first signal associated with an airborne particulate matter concentration in the passenger space;
    a user interface;
    a memory including program instructions stored therein; and
    a controller operably connected to the first particulate matter concentration sensor, the user interface, and the memory and configured to execute the program instructions to
        obtain the first signal,
        identify a cyclical particulate matter concentration pattern based upon the obtained first signal,
        classify the cyclical particulate matter concentration pattern as a smoking event, and
        generate an output using the user interface based upon the classified smoking event.

2. The vehicular airborne particulate matter detection system of claim 1, further comprising:
    a second particulate matter concentration sensor operably connected to the controller and positioned in the passenger space of the vehicle, the second particulate matter concentration sensor configured to generate a second signal associated with the airborne particulate matter concentration in the passenger space, wherein:
    the first particulate matter concentration sensor is located in an upper forward region of the vehicle;
    the second particulate matter concentration sensor is located in an upper rearward region of the vehicle; and
    the controller is further configured to execute the program instructions to
        obtain the second signal, and
        identify the cyclical particulate matter concentration pattern based upon the obtained second signal.

3. The vehicular airborne particulate matter detection system of claim 1, further comprising:
    a third particulate matter concentration sensor located outside of the passenger space and configured to generate a third signal associated with airborne particulate matter concentration outside of the passenger space, wherein:
the controller is further configured to execute the program instructions to
obtain the third signal,
establish an airborne particulate matter concentration threshold based upon the obtained third signal, and
identify the cyclical particulate matter concentration pattern based upon the established airborne particulate matter concentration threshold.

4. The vehicular airborne particulate matter detection system of claim 1, wherein:
the user interface comprises a speaker; and
the controller is configured to execute the program instructions to generate an audible output using the speaker based upon classifying the cyclical particulate matter concentration pattern as a smoking event.

5. The vehicular airborne particulate matter detection system of claim 1, wherein:
the user interface comprises a display; and
the controller is configured to execute the program instructions to generate a visual output using the display based upon classifying the cyclical particulate matter concentration pattern as a smoking event.

6. The vehicular airborne particulate matter detection system of claim 1, wherein at least a portion of the user interface is located remotely from the vehicle.

7. The vehicular airborne particulate matter detection system of claim 1, further comprising:
a camera operably connected to the controller and the memory, wherein
the controller is further configured to execute the program instructions to
capture an image of the passenger space using the camera based upon classifying the cyclical particulate matter concentration pattern as a smoking event, and
store the captured image in the memory.

8. The vehicular airborne particulate matter detection system of claim 1, wherein:
the vehicle includes a window movable between a closed position and at least one open position;
the vehicle includes a window control unit configured to move the window between the closed position and the at least one open position, and to generate a fourth signal associated with a position of the window;
the controller is configured to execute the program instructions to
receive the fourth signal from the window control unit,
establish an airborne particulate matter concentration threshold based upon the obtained fourth signal, and
identify the cyclical particulate matter concentration pattern based upon the established airborne particulate matter concentration threshold.

9. The vehicular airborne particulate matter detection system of claim 1, further comprising:
an airborne particulate matter concentration threshold stored in the memory; and
a camera operably connected to the controller and the memory, wherein
the controller is further configured to execute the program instructions to
compare the obtained first signal to the stored airborne particulate matter concentration threshold,
capture an image of the passenger space using the camera based upon the comparison,
analyze the captured image, and
classify the cyclical particulate matter concentration pattern as a smoking event based upon the analyzed image.

10. The vehicular airborne particulate matter detection system of claim 2, further comprising:
a third particulate matter concentration sensor located outside of the passenger space and configured to generate a third signal associated with airborne particulate matter concentration outside of the passenger space; and
a camera operably connected to the controller and the memory, wherein:
the user interface comprises a speaker, and
the controller is further configured to execute the program instructions to
obtain the third signal,
establish an airborne particulate matter concentration threshold based upon the obtained third signal,
compare the obtained first signal to the established airborne particulate matter concentration threshold,
capture a first image of the passenger space using the camera based upon the comparison,
analyze the captured image,
identify the cyclical particulate matter concentration pattern based upon the established airborne particulate matter concentration threshold,
classify the cyclical particulate matter concentration pattern as a smoking event based upon the analyzed image,
capture a second image of the passenger space using the camera based upon classifying the cyclical particulate matter concentration pattern as a smoking event, and
store the captured second image in the memory.

11. A method of operating a vehicular airborne particulate matter detection system, comprising:
generating with a first particulate matter concentration sensor positioned in a passenger space of a vehicle a first signal associated with an airborne particulate matter concentration in the passenger space;
executing with a controller program instructions stored in a memory to obtain the first signal;
executing the program instructions with the controller to identify a cyclical particulate matter concentration pattern based upon the obtained first signal;
executing the program instructions with the controller to classify the cyclical particulate matter concentration pattern as a smoking event; and
executing the program instructions with the controller to generate an output using the user interface based upon the classified smoking event.

12. The method of claim 11, further comprising:
generating with a second particulate matter concentration sensor positioned in the passenger space of the vehicle a second signal associated with the airborne particulate matter concentration in the passenger space;
executing the program instructions with the controller to obtain the second signal; and
executing the program instructions with the controller to identify the cyclical particulate matter concentration pattern based upon the obtained second signal.

13. The method of claim 11, further comprising:
generating with a third particulate matter concentration sensor positioned outside of the passenger space of the vehicle a third signal associated with the airborne particulate matter concentration in the passenger space;

executing the program instructions with the controller to obtain the third signal;

executing the program instructions with the controller to establish an airborne particulate matter concentration threshold based upon the obtained third signal; and executing the program instructions with the controller to identify the cyclical particulate matter concentration pattern based upon the established airborne particulate matter concentration threshold.

14. The method of claim 11, wherein executing the program instructions with the controller to generate the output comprises:

executing the program instructions with the controller to generate an audible output using a speaker of the user interface based upon classifying the cyclical particulate matter concentration pattern as a smoking event.

15. The method of claim 11, wherein executing the program instructions with the controller to generate the output comprises:

executing the program instructions with the controller to generate a visual output on a display of the user interface based upon classifying the cyclical particulate matter concentration pattern as a smoking event.

16. The method of claim 11, wherein executing the program instructions with the controller to generate the output comprises:

transmitting the output to a portion of the user interface located remotely from the vehicle.

17. The method of claim 11, further comprising:

executing the program instructions with the controller to control a camera operably connected to the controller to capture an image of the passenger space based upon classifying the cyclical particulate matter concentration pattern as a smoking event; and executing the program instructions with the controller to store the captured image in the memory.

18. The method of claim 11, further comprising:

generating with a window control unit configured to move a window of the vehicle between a closed position and at least one open position a fourth signal associated with a position of the window;

executing the program instructions with the controller to receive the fourth signal from the window control unit; and executing the program instructions with the controller to establish an airborne particulate matter concentration threshold based upon the obtained fourth signal, wherein executing the program instructions with the controller to identify the cyclical particulate matter concentration pattern comprises executing the program instructions with the controller to identify the cyclical particulate matter concentration pattern based upon the established airborne particulate matter concentration threshold.

\* \* \* \* \*